United States Patent
Root

(10) Patent No.: US 10,456,160 B2
(45) Date of Patent: Oct. 29, 2019

(54) STENOTIC REGION SCORING ASSEMBLY AND METHOD

(71) Applicant: Teleflex Innovations S.à.r.l., Luxembourg (LU)

(72) Inventor: Howard Root, Excelsior, MN (US)

(73) Assignee: Teleflex Innovations S.à.r.l., Luxembourg (LU)

( * ) Notice: Subject to any disclaimer, the term of this patent is extended or adjusted under 35 U.S.C. 154(b) by 341 days.

(21) Appl. No.: 14/991,065

(22) Filed: Jan. 8, 2016

(65) Prior Publication Data
US 2016/0262789 A1 Sep. 15, 2016

Related U.S. Application Data

(60) Provisional application No. 62/129,997, filed on Mar. 9, 2015.

(51) Int. Cl.
*A61B 17/3207* (2006.01)
*A61B 17/32* (2006.01)

(52) U.S. Cl.
CPC ............... *A61B 17/320725* (2013.01); *A61B 2017/320008* (2013.01)

(58) Field of Classification Search
CPC ........... A61M 29/02; A61B 17/320725; A61B 2017/2215; A61B 2017/00867; A61B 2017/320008
See application file for complete search history.

(56) References Cited

U.S. PATENT DOCUMENTS

| | | | |
|---|---|---|---|
| 5,766,201 A | 6/1998 | Ravenscroft et al. |
| 5,776,578 A | 7/1998 | DeJaynes |
| 5,792,158 A | 8/1998 | Lary |
| 5,797,935 A | 8/1998 | Barath |

(Continued)

FOREIGN PATENT DOCUMENTS

| WO | 2006074256 A1 | 7/2006 |
|---|---|---|
| WO | 2007035888 A2 | 3/2007 |

(Continued)

*Primary Examiner* — Todd J Scherbel
*Assistant Examiner* — Brooke Labranche
(74) *Attorney, Agent, or Firm* — Robert B. Madden

(57) ABSTRACT

Assemblies and methods for scoring a stenotic region within a vessel of a patient are disclosed. An assembly can comprise a scoring member and a deployment member. The scoring member can include an elongate push structure and a tubular, self-expanding scaffold. The elongate push structure can be positioned proximal of the self-expanding scaffold and, at its distal end portion, eccentrically coupled with a proximal end portion of the self-expanding scaffold. The deployment member can be removably positioned within a central lumen of the self-expanding scaffold and detachably engageable with a portion of the self-expanding scaffold. The self-expanding scaffold can be movable between a downsized configuration, when receiving axial tension from the deployment member, and an expanded configuration, in the absence of axial tension. The assembly can further comprise means for detachably engaging the deployment member and the self-expanding scaffold and means for detachably engaging the deployment member and the elongate push structure.

21 Claims, 6 Drawing Sheets

(56) References Cited

U.S. PATENT DOCUMENTS

| | | |
|---|---|---|
| 6,059,812 A | 5/2000 | Clerc et al. |
| 6,254,571 B1 | 7/2001 | Hart |
| 6,951,566 B2 | 10/2005 | Lary |
| 7,390,298 B2 | 6/2008 | Chu |
| 7,522,950 B2 | 4/2009 | Fuimaono et al. |
| 7,556,641 B2 | 7/2009 | Cully et al. |
| 7,655,026 B2 | 2/2010 | Justis et al. |
| 7,771,446 B2 | 8/2010 | Rutter |
| 8,123,770 B2 | 2/2012 | Olsen et al. |
| 8,231,668 B2 | 7/2012 | Friebe et al. |
| 8,439,961 B2 | 5/2013 | Jagger et al. |
| 8,690,903 B2 | 4/2014 | Bence et al. |
| 8,771,299 B2 | 7/2014 | Diamant et al. |
| 8,771,305 B2 | 7/2014 | Shriver |
| 2002/0049452 A1 | 4/2002 | Kurz et al. |
| 2004/0236186 A1 | 11/2004 | Chu |
| 2005/0080478 A1 | 4/2005 | Barongan |
| 2006/0030843 A1 | 2/2006 | Lane et al. |
| 2006/0178685 A1 | 8/2006 | Melsheimer |
| 2007/0106215 A1* | 5/2007 | Olsen ............ A61B 17/320725 604/96.01 |
| 2008/0167608 A1 | 7/2008 | Rutter |
| 2009/0030288 A1 | 1/2009 | Abboud et al. |
| 2009/0264859 A1 | 10/2009 | Mas |
| 2010/0087850 A1 | 4/2010 | Razack |
| 2010/0286722 A1 | 11/2010 | Rizk et al. |
| 2012/0101561 A1 | 4/2012 | Porter |
| 2012/0215251 A1 | 8/2012 | Burton et al. |
| 2012/0232638 A1 | 9/2012 | Diamant et al. |
| 2013/0041391 A1* | 2/2013 | Spencer ......... A61B 17/320725 606/159 |
| 2013/0066346 A1 | 3/2013 | Pigott |
| 2013/0110142 A1 | 5/2013 | Bence et al. |
| 2014/0128895 A1 | 5/2014 | Bence et al. |
| 2014/0142408 A1 | 5/2014 | Rama et al. |
| 2014/0163594 A1 | 6/2014 | Schur et al. |
| 2014/0257352 A1 | 9/2014 | Weber et al. |
| 2014/0257369 A1 | 9/2014 | Leopold et al. |
| 2014/0277359 A1 | 9/2014 | Slazas et al. |

FOREIGN PATENT DOCUMENTS

| | | |
|---|---|---|
| WO | 2007053728 A1 | 5/2007 |
| WO | 2008148041 A1 | 12/2008 |
| WO | 2009117563 A2 | 9/2009 |
| WO | 2013040160 A1 | 3/2013 |
| WO | 2014112856 A1 | 7/2014 |

* cited by examiner

STENOTIC REGION SCORING ASSEMBLY AND METHOD

CLAIM OF PRIORITY

This non-provisional patent document claims the benefit of priority under 35 U.S.C. § 119(e) to U.S. Provisional Patent Application Ser. No. 62/129,997, entitled "STENOTIC REGION SCORING ASSEMBLY AND METHOD" and filed on Mar. 9, 2015, which is herein incorporated by reference in its entirety.

TECHNICAL FIELD

This patent document relates to medical devices. More particularly, but not by way of limitation, the patent document relates to assemblies and methods for treating a stenotic region in a vessel.

BACKGROUND

Stenotic regions in vessels of a patient can develop for a variety of reasons and can have different adverse effects on the patient. Stenotic regions can occur within multiple vessels of the same organ or can occur as a series of regions within the same vessel. Stenotic regions can be singular or multiple. Depending on the location of a particular stenotic region, the patient can experience cardiac arrest, stroke, or tissue or organ necrosis. The severity of damage to the patient can depend on the nature of the stenotic region and the extent of its development.

Angioplasty is one of several types of medical procedures that have been used to surgically dilate a stenotic region in a vessel. An angioplasty procedure involves the use of a dilatation balloon catheter. The catheter is advanced, using fluoroscopy, over a guidewire so that the catheter's dilatation balloon is positioned within the stenotic region. The dilatation balloon is then inflated to apply radial pressure to the stenotic material and adjacent inner wall portions of the vessel, thereby clearing the stenotic region to enable better blood flow.

Overview

The present inventor recognizes that the treatment efficacy of stenotic regions can be enhanced by scoring or otherwise cutting the material that is creating the stenotic region, in addition to dilation. After scoring, a stenotic region is more easily flattened during dilation, thereby inhibiting restenosis and reducing the likelihood of vessel damage. The present inventor further recognizes that it can be desirable to provide an intravascular assembly including an expandable scoring member that is selectively controllable by a physician and, when in an expanded configuration, able to receive off-the-shelf dilatation balloons of various longitudinal or diametrical sizes.

The present assemblies can include a scoring member and a deployment member. The scoring member can include an elongate push structure and a tubular, self-expanding scaffold to facilitate scoring, fragmentation or other cutting of stenotic material. The elongate push structure is positioned proximal of the self-expanding scaffold and, at its distal end portion, can be eccentrically coupled with a proximal end portion of the self-expanding scaffold. The deployment member can be removably positioned within a central lumen of the self-expanding scaffold and detachably engageable with a portion of the self-expanding scaffold to selectively control its radial configuration. The self-expanding scaffold can be movable between a downsized configuration, when receiving axial tension from the deployment member, and an expanded configuration, in the absence of axial tension. In the expanded configuration, the self-expanding scaffold can receive various sizes of dilatation balloons. The assembly can further comprise means for detachably engaging the deployment member and the self-expanding scaffold and means for detachably engaging the deployment member and the elongate push structure.

The present methods for scoring a stenotic region within a vessel of a patient can include accessing the vessel by piercing an opening; inserting a guidewire into the opening and advancing the guidewire toward or past the stenotic region; inserting a delivery sheath into the vessel; advancing an assembly for scoring the stenotic region through the delivery sheath and toward the stenotic region, the assembly including a self-expanding scaffold and a deployment member positioned within a central lumen of the self-expanding scaffold, the deployment member applying axial tension to a self-expanding scaffold to maintain a radially downsized configuration; removing the deployment member from the self-expanding scaffold, including allowing the self-expanding scaffold to expand from the radially downsized configuration to a radially expanded configuration; advancing a deflated dilatation balloon of a catheter over the guidewire and into the central lumen of the self-expanding scaffold; and inflating the dilatation balloon to press against the interior of the self-expanding scaffold and urge the outer surface of the self-expanding scaffold into the stenotic region.

These and other examples and features of the present assemblies and methods will be set forth, at least in part, in the following Detailed Description. This Overview is intended to provide non-limiting examples of the present subject matter—it is not intended to provide an exclusive or exhaustive explanation. The Detailed Description below is included to provide further information about the present assemblies and methods.

BRIEF DESCRIPTION OF THE DRAWINGS

In the drawings, like numerals can be used to describe similar features and components throughout the several views. The drawings illustrate generally, by way of example but not by way of limitation, various embodiments discussed in the present patent document.

Figure 1:
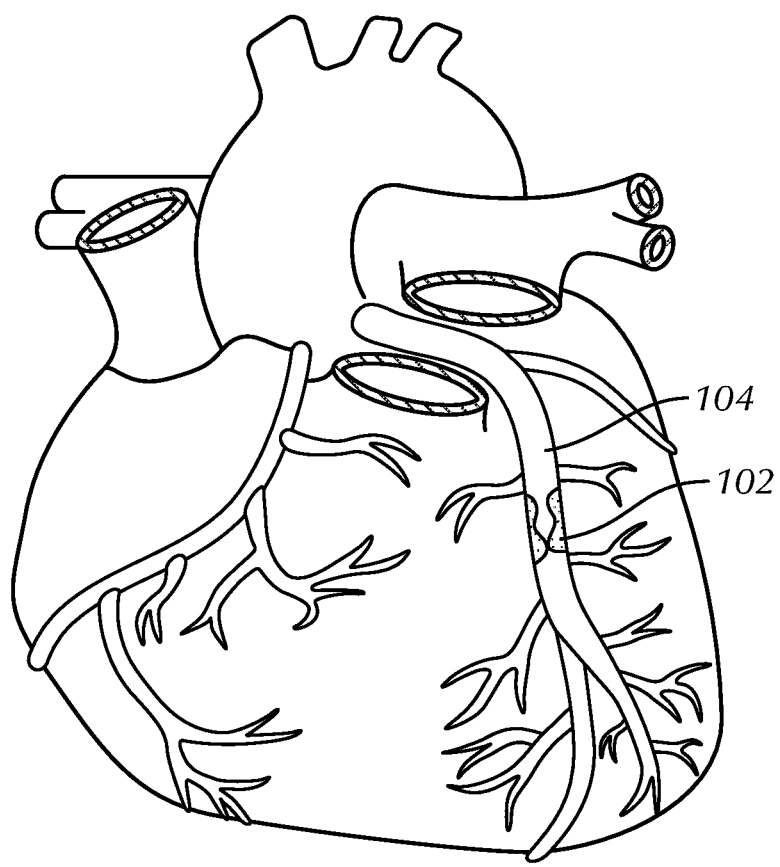
FIG. 1 illustrates a stenotic region located in a coronary vessel.

The drawing figures are not necessarily to scale. Certain features and components may be shown exaggerated in scale or in schematic form, and some details may not be shown in the interest of clarity and conciseness.

DETAILED DESCRIPTION

Figure 2:
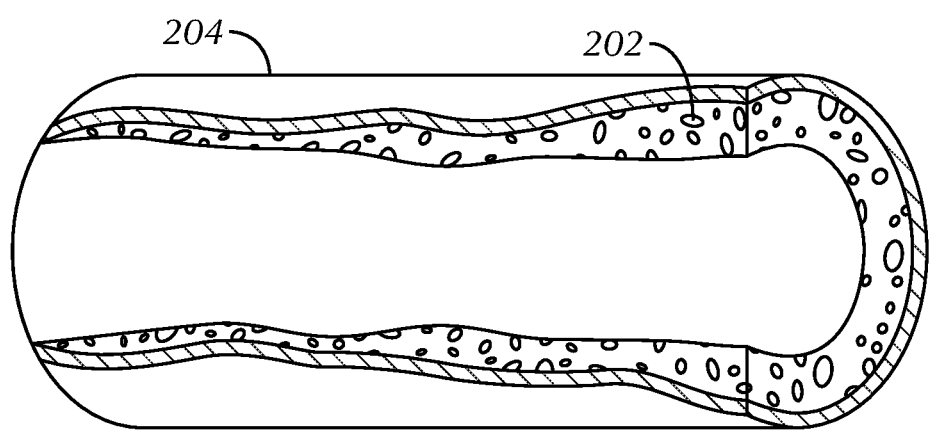
FIG. 2 illustrates an enlarged view of the stenotic region of FIG. 1.

FIG. 1 illustrates a stenotic region 102 located in a coronary vessel 104, and FIG. 2 illustrates an enlarged view of a stenotic region 202 in a coronary vessel 204. While the present assemblies and methods can find use in the treatment of coronary vessels, it is to be understood that use of the assemblies and methods is not limited to coronary or upper body vessels and can be used in vessels throughout the body.

Figure 3:
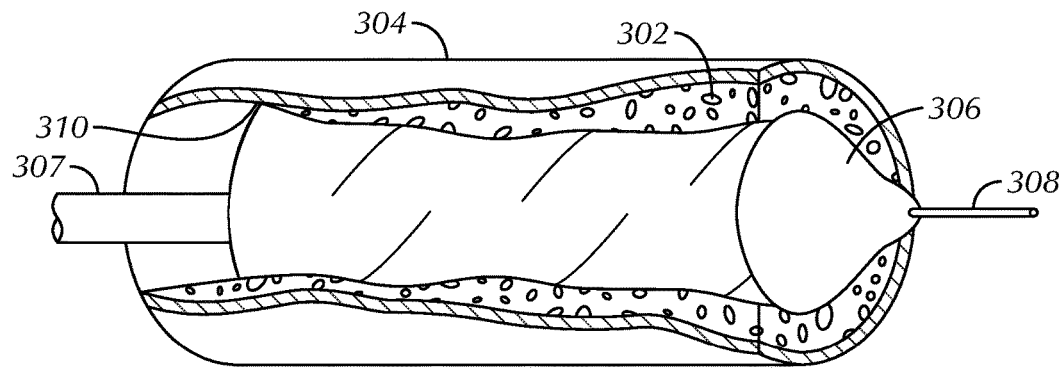
FIG. 3 schematically illustrates a dilatation balloon of a catheter advanced over a guidewire, positioned within the stenotic region of FIG. 2, and inflated to apply radial pressure to the stenotic material.
Figure 4:
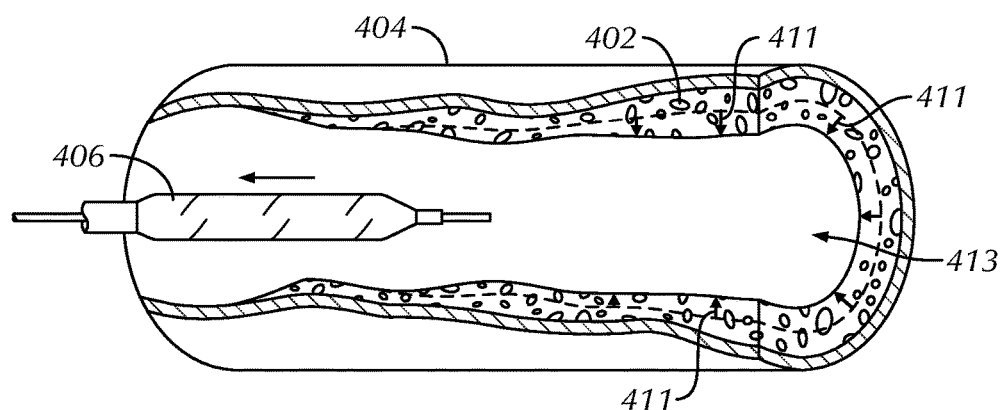
FIG. 4 illustrates restenosis of the stenotic region dilated by the catheter in FIG. 3.

The stenotic region 102, 202 can include areas of fibrotic, calcified or otherwise hardened plaque or other stenotic material of a type difficult to treat using a dilatation balloon alone. For example, FIG. 3 illustrates a schematic view of a dilatation balloon 306 of a catheter 307 advanced over a guidewire 308, positioned within a stenotic region 302, and inflated to apply radial pressure to the stenotic material and adjacent inner wall 310 portions of a vessel 304. When the dilatation balloon 406 is deflated and removed from the vessel 404, the stenotic region 402 can rebound 411 and shrink the size of the enlarged opening 413 that was temporarily created through dilation, as shown in FIG. 4.

Figure 5:
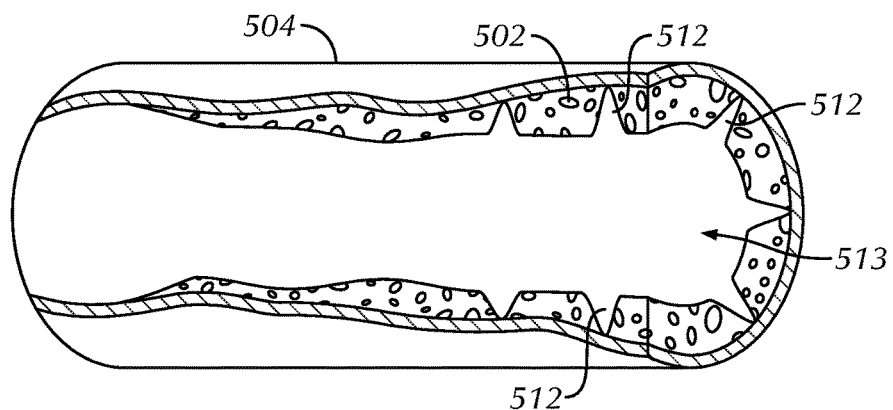
FIG. 5 illustrates reduction in restenosis of the stenotic region of FIG. 2 through concurrent scoring and dilation using a present assembly or method.

FIG. 5 illustrates that treatment efficacy of a stenotic region 502 can be enhanced by scoring or otherwise cutting 512 the material that is creating the stenotic region 502, in addition to dilation. When the dilatation balloon is deflated and removed from the vessel 504 following scoring and dilation, the stenotic region 502 can maintain its enlarged opening 513.

Figure 6:
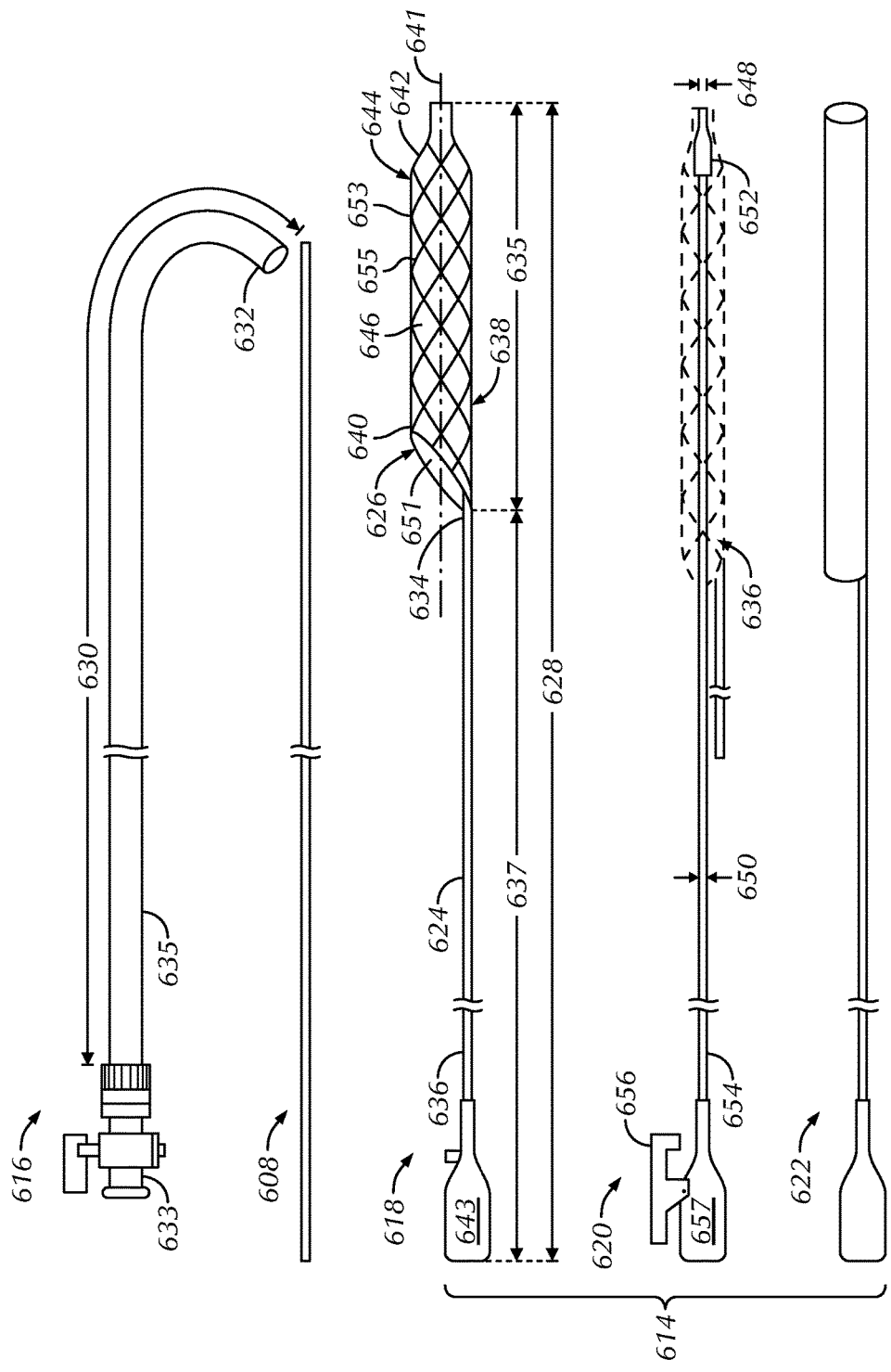
FIG. 6 illustrates a side view of a delivery sheath, a guidewire and a present assembly, including a scoring member, a deployment member and a recovery tube, as constructed in accordance with at least one embodiment.

FIG. 6 illustrates components of a present assembly 614 configured to incise calcified, fibrotic and other hard stenotic regions and leave scores or grooves during a dilation procedure. After gaining access to a vessel of interest by piercing an opening, a guidewire 608 can be inserted into the vessel and advanced toward or past a stenotic region, and a delivery sheath 616 can be guided over the guidewire 608 and into the vessel. The delivery sheath 616 can have a proximal end portion 633 and a distal end portion 632 and can define a lumen 635 through which components of the assembly 614, including a scoring member 618, a deployment member 620 and an optional recovery tube 622, can be guided to the stenotic region at various times during a procedure.

The scoring member 618 can include an elongate push structure 624 and a tubular, self-expanding scaffold 626. The scoring member 618 can have a collective length 628 greater than a length 630 of the delivery sheath 616 to allow the self-expanding scaffold 626 to extend beyond the distal end 632 of the delivery sheath 616 and the elongate push structure 624 to extend beyond the proximal end 633 of the delivery sheath 616. In an example, the self-expanding scaffold 626 can have a length 635 in a range of about 10 cm to about 30 cm, inclusive, and the elongate push structure 624 can have a length 637 in a range of about 100 cm to about 200 cm, inclusive. Scoring of the stenotic region can be accomplished by positioning the self-expanding scaffold 626 within the stenotic region using the elongate push structure 624, inserting a dilatation balloon or other expandable member within the scaffold 626, and inflating the dilatation balloon or other expandable member to urge the scaffold 626 radially outward, causing scores or grooves in the stenotic region.

The elongate push structure 624 is positioned proximal of the self-expanding scaffold 626 and can be eccentrically coupled with the scaffold on its distal end portion 634, such as attached to the self-expanding scaffold 626 at a peripheral location offset from a central longitudinal axis 641. This eccentric coupling provides a greater working area within the delivery sheath 616. The distal end portion 634 of the elongate push structure 624 can be flattened to provide sufficient surface area to secure to the self-expanding scaffold 626. The proximal end portion 636 of the elongate push structure 624 can include a handle 643 to facilitate manipulation of the scoring member 618 through the delivery sheath 616 and to the stenotic region. The elongate push structure 624 can have sufficient rigidity to be pushed distally (i.e., apply an axially compressive force) and pulled proximally (i.e., apply an axially tensile force) to manipulate the self-expanding scaffold 626. The elongate push structure 624, which can be a tubular member or a solid member, can extend through the lumen 635 of the delivery sheath 616, adjacent and generally parallel to the guidewire 608.

The self-expanding scaffold 626 can be movable between a downsized configuration 636, facilitating insertion of the scoring member 618 through the delivery sheath 616 and into the vessel, when receiving axial tension from the deployment member 620, and an expanded configuration 638, facilitating contact with a stenotic material and allowing for receipt of a dilatation balloon of a catheter, in the absence of axial tension. The self-expanding scaffold 626 can have any desired construction (e.g., coiled or braided) permitting it to be radially compressed into the downsized configuration 636 and radially enlarged to the expanded configuration 638. The braid or coil members can maintain a more parallel relationship with the central longitudinal axis 641 of the self-expanding scaffold 626 in the elongated, downsized configuration 636 than in the expanded configuration 638. The self-expanding scaffold 626 can be formed from any number of biocompatible materials, including polymeric materials, metals, and metal alloys, such as stainless steel, platinum alloy, tantalum, or a nickel titanium alloy such as a superelastic nickel titanium alloy (also known as nitinol). Metallic materials advantageously provide radiopacity under fluoroscopy, and superelastic materials or shape memory materials are advantageously elongatable without permanent deformation (e.g., can undergo deformation under the influence of force, but then spring back to an original shape after the force is removed).

The proximal end portion 640 of the self-expanding scaffold 626 can include a proximal opening 651 into a central lumen 646 of the scaffold, permitting receipt and positioning of a dilatation balloon of a catheter. In some examples, the self-expanding scaffold 626 can include an annular hoop at the proximal end portion 640 to define the proximal opening 651. In other examples, the proximal end portion 640 can include an angled proximal opening 651 providing a larger area (than the annular hoop) to receive the dilatation balloon.

Figure 7:
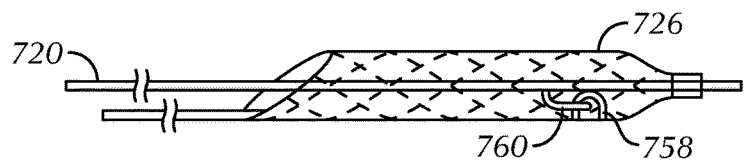
FIG. 7 schematically illustrates engagement between portions of a present assembly, specifically a distal end portion of a self-expanding scaffold and a distal end portion of a deployment member, as constructed in accordance with at least one embodiment.

The distal end portion 642 of the self-expanding scaffold 626 can include a configuration to engage with one or both of the deployment member 620 or the dilatation balloon. For example, the distal end portion 642 can include a funnel structure 644 sized and shaped to receive the distal end portion 652 of the deployment member 620 for receipt of axial tension. The funnel structure 644 can also be used as a stopper to properly position and align the dilatation balloon within the self-expanding scaffold 626 after the deployment member 620 is removed; in this way, the dilatation balloon can be inserted into the self-expanding scaffold 626 until its distal end abuts against the funnel structure 644. The funnel structure 644 can further advantageously provide a shape that facilitates insertion of the self-expanding scaffold 626 through the delivery sheath 616 and into the stenotic region. As one alternative to the funnel structure 644, the self-expanding scaffold 726 can include a projection 758 sized and shaped to engage with a projection 760 of the deployment member 720, as shown by way of example in FIG. 7. The projection 758 of the scaffold can be in the form of a hook sized and shaped to engage with the projection 760 of the deployment member 720 in the form of a finger.

Referring again to FIG. 6, the central lumen 646 of the self-expanding scaffold 626 can be sized and shaped to receive an off-the-shelf dilatation balloon of various longitudinal or diametrical sizes. During a procedure, the dilatation balloon can be received into the self-expanding scaffold 626 and inflated, thereby causing an outer surface 653 of the scaffold to move radially outward and contact the stenotic region. The outer surface 653 of the self-expanding scaffold 626 can include a plurality of scoring edges or elements 655.

The deployment member 620 can be slidably receivable within the central lumen 646 of the self-expanding scaffold 626 and detachably engageable with a portion of the scaffold 626 to create the downsized configuration 636. The distal end portion 652 of the deployment member 620 can include a blunt tip engageable with the funnel structure 644, for example, and the proximal end portion 654 can include a handle 657 and an optional latch member 656. When fully inserted into the self-expanding scaffold 626, the deployment member 620 can axially stretch the tubular body of the scaffold 626 into the downsized configuration 636, as shown in phantom. The latch member 656 can engage with the proximal end portion 636 of the elongate push structure 624 to maintain the self-expanding scaffold 626 in the downsized configuration 636 during delivery to the stenotic region. When desired, the self-expanding scaffold 626 can be released from the axial force of the deployment member 620 by depressing the latch member 656, and the scaffold 626 can be free to shorten and radially enlarge as a result of its elastic nature. Although shown as a pivoting member at the proximal end portion 654 of the deployment member 620, the latch member 656, if present, can take many other forms and be located elsewhere on the deployment member 620 and/or the scoring member 618 provided that it relatively locks the deployment member 620 and the scoring member 618. The deployment member 620 can be in the form of a dilator or a stylet and can include an inner wire lumen 648 having a diameter in a range of about 0.014 in to about 0.018 in, inclusive, and an outer surface diameter 650 in a range of about 0.020 in to about 0.030 in, inclusive.

After scoring and dilating the stenotic region, the scoring member 618 can be removed from the vessel. The self-expanding scaffold 626 can be moved from the expanded configuration 638 to the downsized configuration 636 by reinserting the deployment member 620 into the scaffold's central lumen 646 or by advancing the optional recovery tube 622 over the scaffold. The recovery tube 622 can optionally taper in a distal-to-proximal direction to facilitate radially contracting the self-expanding scaffold 626 as it is drawn into the tube.

FIGS. 8-14 illustrate a method for scoring and dilating stenotic regions within a vessel using a present assembly.

Figure 8:
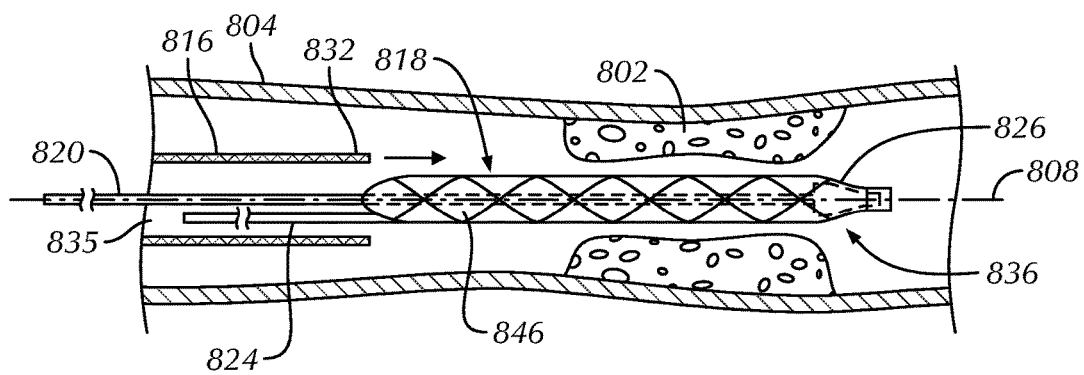
FIG. 8 schematically illustrates a scoring member and a deployment member being delivered into a vessel over a guidewire and through a delivery sheath, as constructed in accordance with at least one embodiment.

FIG. 8 schematically illustrates a scoring member 818, including a self-expanding scaffold 826 and an elongate push structure 824, and a deployment member 820 being delivered into a vessel 804 over a guidewire 808 and through a delivery sheath 816. Access to the vessel 804 can be obtained by piercing an opening in a peripheral artery, such as the femoral artery. Next, the guidewire 808 can be inserted into the opening and advanced through the patient's vasculature. The guidewire 808 can be advanced and steered into the vessel 804 of interest and then advanced past the stenotic region 802 requiring treatment. The delivery sheath 816 can be inserted into the vessel 804 and over the guidewire 808, with the guidewire 808 extending through a lumen 835 of the sheath.

With the deployment member 820 positioned within a central lumen 846 of the self-expanding scaffold 826, distal end portions of the self-expanding scaffold 826 and the deployment member 820 can be inserted over the guidewire 808 and advanced through the delivery sheath 816 toward the stenotic region 802. The deployment member 820 can apply axial tension to the self-expanding scaffold 826 and, upon being fully received by the scaffold 826, the proximal end portion of the deployment member 820 can be latched to the proximal end portion of the elongate push structure 824, for example. This maintains the self-expanding scaffold 826 in a radially downsized configuration 836. The guidewire 808 can extend along and adjacent to the elongate push member 824 within the lumen 835 of the delivery sheath 816. The self-expanding scaffold 826 can be advanced beyond the distal end 832 of the delivery sheath 816 and positioned within the stenotic region 802.

Figure 9:
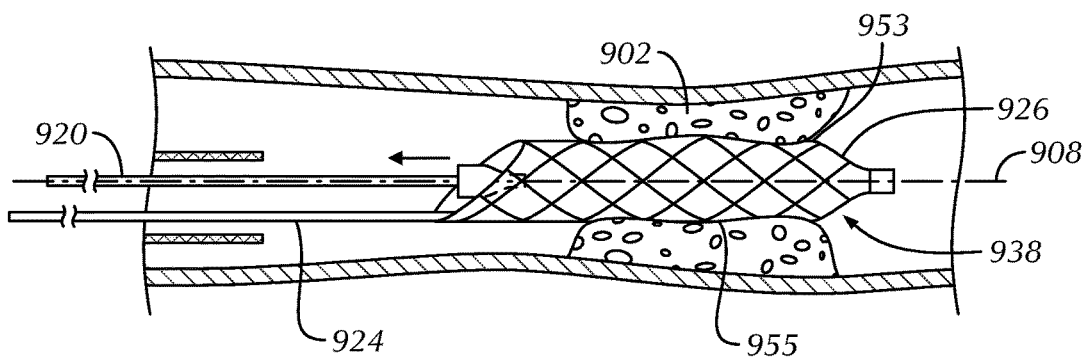
FIG. 9 schematically illustrates a deployment member being removed from a self-expanding scaffold, which allows the self-expanding scaffold to expand, as constructed in accordance with at least one embodiment.

FIG. 9 schematically illustrates a deployment member 920 being removed over a guidewire 908 from a self-expanding scaffold 926, which allows the self-expanding scaffold 926 to expand from a radially downsized configuration to a radially expanded configuration 938. The physician can hold a proximal end portion of the elongate push structure 924 while pulling a proximal end portion of the deployment member 920 to maintain the self-expanding scaffold 926 in a desired position relative to a stenotic region 902. Once unconstrained by the deployment member 920, the self-expanding scaffold 926 can automatically radially enlarge toward the expanded configuration 938. The self-expanding scaffold 926 can be sized such that in the expanded configuration 938, scoring edges or elements 955 on an outer surface 953 of the self-expanding scaffold 926 can contact and press against the stenotic region 902.

Figure 10:
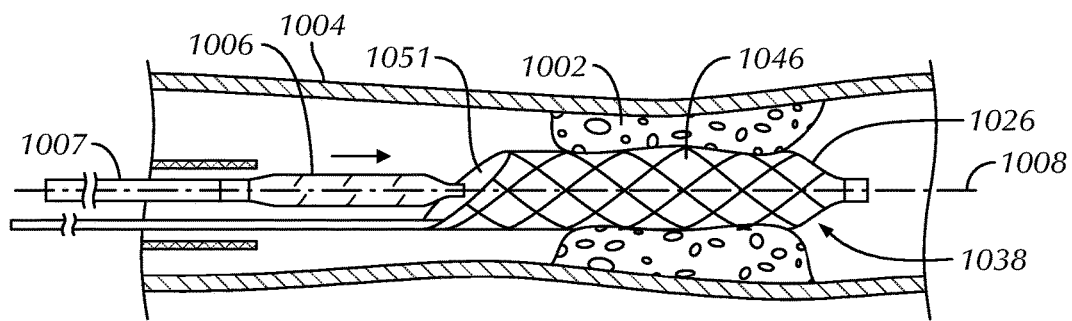
FIG. 10 schematically illustrates the advancement of a deflated dilatation balloon of a catheter over a guidewire, through a proximal opening and into a central lumen of a self-expanding scaffold, as constructed in accordance with at least one embodiment.

FIG. 10 schematically illustrates the advancement of a deflated dilatation balloon 1006 of a catheter 1007 over a guidewire 1008, through a proximal opening 1051 and into a central lumen 1046 of a self-expanding scaffold 1026 in a radially expanded configuration 1038. The proximal opening 1051 can be angled to allow for easier passage of the dilatation balloon 1006 into the central lumen 1046 of the self-expanding scaffold 1026.

The dilatation balloon 1006 can be selected by the physician based on the desired inflated diameter of the balloon 1006 for a particular medical procedure. For example, the dilatation balloon 1006 may be selected based on the diameter of the vessel 1004 to be treated, the size of the stenotic region 1002, or the amount of radial expansion of the self-expanding scaffold 1026 desired. The dilatation balloon 1006 can, for example, be constructed from polyurethane, silicone or some other suitable biocompatible material. A diameter of the dilatation balloon 1006 can, for example, be from in a range of about 4 mm to about 20 mm, inclusive, for use in the venous system and from about 1.5 mm to about 12 mm, inclusive, for use in the arterial system.

Figure 11:
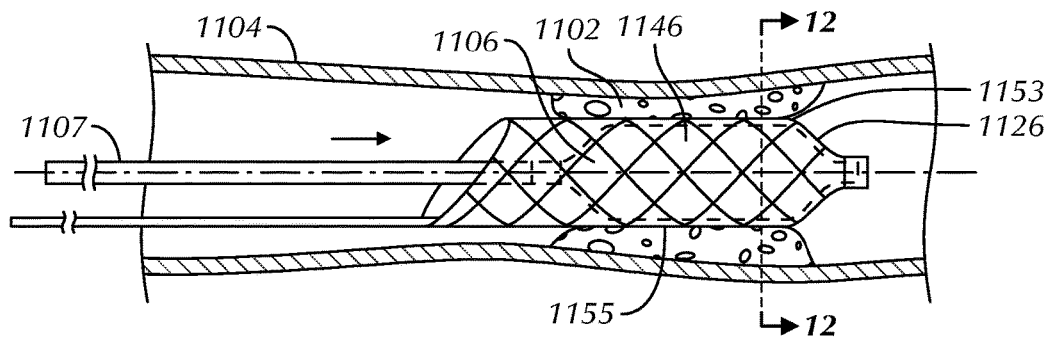
FIG. 11 schematically illustrates inflation of a dilatation balloon of a catheter and an urging of an outer surface of a self-expanding scaffold into a stenotic region, as constructed in accordance with at least one embodiment.

FIG. 11 schematically illustrates inflation of a first dilatation balloon 1106 of a catheter 1107 and an urging of an outer surface 1153 of a self-expanding scaffold 1126 into a stenotic region 1102. Once positioned within a central lumen 1146 of the self-expanding scaffold 1126, the first dilatation balloon 1106 can be inflated to exert a radially outward force on the interior of the scaffold 1126 to further enlarge the scaffold and urge scoring edges or elements 1155 on the outer surface 1153 of the scaffold 1126 further radially outward to penetrate into the stenotic region 1102. The scoring edges or elements 1155 can cut or score the stenotic region 1102 to facilitate enlarging the region. Each scoring edge or element 1155 can define a focal point or a radial plane of fracture on the stenotic region 1102 whereat lacerations are formed. Upon contact with the stenotic region 1102, the scoring edge or element 1155 can break the stenotic material in a relatively organized fashion, lessening the likelihood of restenosis in the region 1102 of the vessel 1104.

Varying options are possible to facilitate scoring the stenotic region 1102 with the self-expanding scaffold 1126. For example, the first dilatation balloon 1106 can be deflated and the self-expanding scaffold 1126 can be rotated for subsequent transverse movement of the first dilatation balloon 1106 and scaffold 1126 into contact with the same or another stenotic region. Or, the first dilatation balloon 1106 can be deflated and removed from the self-expanding scaffold 1126, and a second dilatation balloon of a different size can be advanced into the central lumen 1146 of the scaffold 1126 and inflated. For example, the first dilatation balloon 1106 can have a first inflated diameter and the second dilatation balloon can have a second inflated diameter greater than the inflated diameter of the first dilatation balloon 1106. Thus, the first dilatation balloon 1106 can be used to radially expand the expandable scaffold 1126 to a first diameter and urge the scoring edges or elements 1155 into the stenotic region 1102 a first amount, and then the first dilatation balloon 1106 can be exchanged for the second dilatation balloon to further expand the expandable scaffold 1126 to a second diameter greater than the first diameter and urge the scoring edges or elements 1155 further into the stenotic region 1102 a second amount, greater than the first amount. The first and second dilatation balloons can be sequentially exchanged for balloons of a different size (e.g., of a sequentially greater size) until a desired dilatation of the vessel 1104 has been attained.

Figure 12:
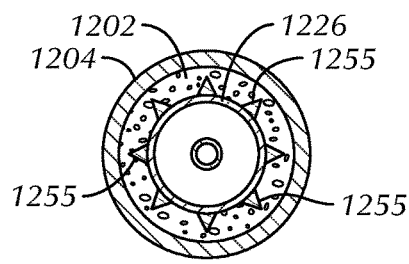
FIG. 12 schematically illustrates, in cross-section along line 12-12 in FIG. 11, the urging of scoring edges or elements of a self-expanding scaffold into a stenotic region when a dilatation balloon of a catheter is inflated, as constructed in accordance with at least one embodiment.

FIG. 12 schematically illustrates, in cross-section along line 12-12 in FIG. 11, urging scoring edges or elements 1255 of a self-expanding scaffold 1226 into a stenotic region 1202 when an inner dilatation balloon 1206 is inflated. Each scoring edge or element 1255 of the self-expanding scaffold 1226 can expand along its respective radial plane of fracture to engage the stenotic region 1202 in the vessel 1204. Upon contact with the stenotic region 1202, the scoring edges or elements 1255 can break the stenotic material in a relatively organized fashion. It has been found that as the dilatation balloon 1206 pushes the stenotic material radially outwardly, the scoring edges or elements 1255 cut and allow the material to be folded for further dilatation of the vessel 1204. Furthermore, trauma to the stenotic material caused by the scoring edges or elements 1255 results in relatively organized lacerations that minimize or lessen the likelihood of restenosis in the stenotic region 1202 of the vessel 1204. Thus, the lacerations formed on the stenotic material allow for a relatively more effective treatment of stenotic region 1202.

The scoring edges or elements 1255 of the self-expanding scaffold 1226 can have a cross-sectional dimension and shape to cut or score a calcinated and other hard stenosed material during the dilation procedure. For example, the scoring edges or elements 1255 can each have a cross-sectional dimension in the range of about 0.01 mm to about 0.5 mm, inclusive. The cross-sectional shape and dimension of the scoring edges or elements 1255 can vary from wire-to-wire composing the scaffold 1226 or along the lengths of each wire. The cross-section of at least a part of the scoring edge or element 1255 can, for example, have a triangle shape, circular shape, oval shape, D-shape, rectangular shape, polygonal or any other appropriate shape that can cut or score calcinated and other hard stenotic materials within the vessel 1204 during the dilation procedure. The outer periphery of the scoring edge or element 1255 can be formed with a grinding process, laser cutting or by another suitable method to provide a smooth profile, and desired shapes, tapers and changes in dimension.

The scoring edges or elements 1255 can vary in number, position, and arrangement about the self-expanding scaffold 1226. For example, the self-expanding scaffold 1226 can include one, two, three, four, five, six or more scoring edges or elements 1255 that are disposed at any position along the self-expanding scaffold 1226 and in a regular, irregular, or any other suitable pattern. For example, the self-expanding scaffold 1226 can include a plurality of scoring edges or elements 1255 longitudinally arranged symmetrically around the circumference of the scaffold 1226.

In order to prevent restenosis in the stenotic region 1202, the self-expanding scaffold 1226 can comprise an active pharmacologic agent that can be delivered to a wall of the vessel 1204 cut or scored. A wide variety of active pharmacologic agents that can effectively inhibit inflammation and smooth-muscle cell growth are known. Examples of such pharmacologic agents include, but are not limited to, anti-proliferative agents, immunomodulators, anti-thrombotics, and growth factor inhibitors. The active pharmacologic agents can be provided on or within the self-expanding scaffold 1226 in a variety of ways. For example, the active agents may be coated over at least a portion of a surface of the self-expanding scaffold 1226 through dipping, spraying, painting, plasma deposition, electroplating, ink-jet coating, centrifuge systems or the like.

Figure 13:
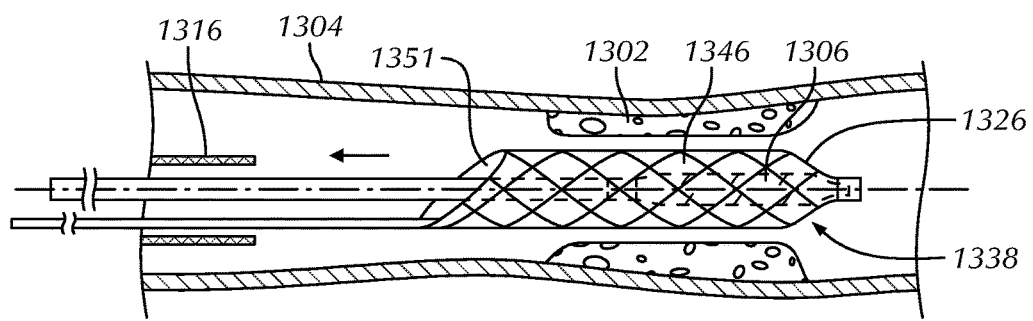
FIG. 13 schematically illustrates a deployment member reinserted into a central lumen of a self-expanding scaffold for retrieval of the self-expanding scaffold from a vessel, as constructed in accordance with at least one embodiment.

After the stenotic region 1302 has been dilated, the dilatation balloon 1306 can be deflated, as schematically illustrated in FIG. 13. Upon deflation of the dilatation balloon 1306, the self-expanding scaffold 1326 may no longer be in contact with an outer surface of the balloon, thereby allowing the dilatation balloon 1306 to be withdrawn from a central lumen 1346 through a proximal opening 1351. The self-expanding scaffold 1326 can then be urged from a radially expanded configuration 1338 to a radially downsized configuration, recaptured and retrieved through a delivery sheath 1316, and withdrawn from the vessel 1304. For example, as schematically illustrated in FIG. 8, a deployment member can be inserted into the central lumen of the self-expanding scaffold to urge the scaffold to a radially downsized configuration and retrieved through the delivery sheath.

Figure 14:
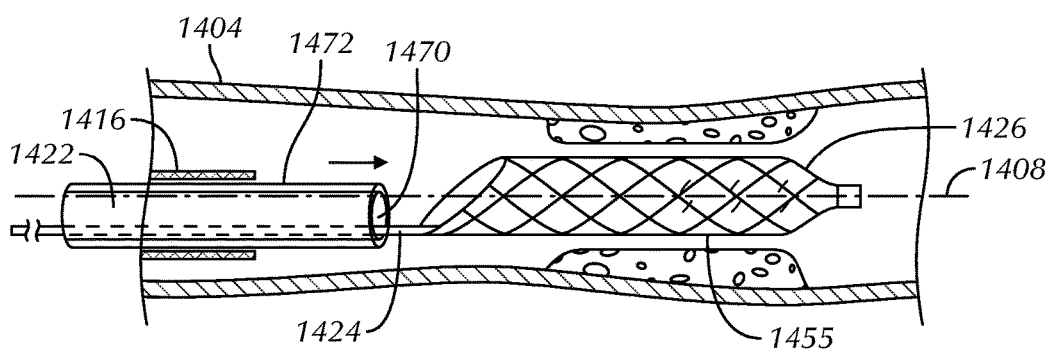
FIG. 14 schematically illustrates a recovery tube inserted over a self-expanding scaffold to remove the self-expanding scaffold from a vessel, as constructed in accordance with at least one embodiment.

Or, as schematically illustrated in FIG. 14, a recovery tube 1422 can be inserted over a self-expanding scaffold 1426 and collectively removed from the vessel 1404. The physician can grasp an elongate push structure 1424 to hold the self-expanding scaffold 1426 stationary while advancing the recovery tube 1422 distally over the scaffold 1426 to collapse the scaffold into a lumen 1470 of the tube 1422, or the physician can pull the elongate push structure 1426 proximally to pull the self-expanding scaffold 1426 into a distal opening 1472 of the recovery tube 1422 to collapse the scaffold 1426 into the lumen 1470. Inadvertent contact between the scoring edges or elements 1455 of the self-expanding scaffold 1426 and the vessel 1404 is prevented during withdrawal by the delivery sheath 1416 or the recovery tube 1422. The delivery sheath 1416 or recovery tube 1422 and the self-expanding scaffold 1426 can be withdrawn from the vessel 1404, leaving the guidewire 1408 in place for navigating additional medical devices across the stenotic region 1402 in the vessel 1404, if desired.

Closing Notes:

The present assemblies and methods offer many advantages for treating a stenotic region in a vessel to increase blood flow through the conduit. For example, an assembly's scoring member can be selectively controllable by a physician and, when in an expanded configuration, able to receive dilatation balloons of various longitudinal or diametrical sizes. This allows the physician to use standard, off-the-shelf dilatation balloons with a single scoring member based on a desired amount of dilation. The concurrent dilation and scoring technique of the present assemblies and methods can also minimize the vascular trauma incurred during angioplasty, because a lower balloon pressure can be applied when a dilatation balloon is surrounded by a scoring member compared to using a dilatation balloon alone.

The above Detailed Description includes references to the accompanying drawings, which form a part of the Detailed Description. The Detailed Description should be read with reference to the drawings. The drawings show, by way of illustration, specific embodiments in which the present assemblies and methods can be practiced. These embodiments are also referred to herein as "examples."

The above Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, an assembly for scoring a stenotic region within a vessel of a patient can comprise a scoring member and a deployment member. The scoring member can include an elongate push structure and a tubular, self-expanding scaffold. The elongate push structure can be positioned proximal of the self-expanding scaffold and, at its distal end portion, eccentrically coupled with a proximal end portion of the self-expanding scaffold. The deployment member can be removably positioned within a central lumen of the self-expanding scaffold and detachably engageable with a portion of the self-expanding scaffold. The self-expanding scaffold can be movable between a downsized configuration, when receiving axial tension from the deployment member, and an expanded configuration, in the absence of axial tension.

In Example 2, the assembly of Example 1 can optionally be configured such that the proximal end portion of the self-expanding scaffold includes an angled opening sized and shaped to receive the deployment member or an expandable member of a catheter when the self-expanding scaffold is positioned within the vessel.

In Example 3, the assembly of any one or any combination of Examples 1 or 2 can optionally be configured such that a distal end portion of the self-expanding scaffold includes a funnel structure sized and shaped to receive, and detachably engage, a distal end portion of the deployment member.

In Example 4, the assembly of any one or any combination of Examples 1 or 2 can optionally be configured such that a distal end portion of the self-expanding scaffold includes a projection sized and shaped to engage a projection of a distal end portion of the deployment member.

In Example 5, the assembly of any one or any combination of Examples 1-4 can optionally be configured such that the self-expanding scaffold includes a plurality of braid members or a coil member. The braid members or the coil member can maintain a more parallel relationship with an axis of the scoring member in the downsized configuration than in the expanded configuration.

In Example 6, the assembly of Example 5 can optionally be configured such that an outer surface of at least one braid member or the coil member is configured to cut into or score the stenotic region within the vessel.

In Example 7, the assembly of any one or any combination of Examples 1-6 can optionally be configured such that the self-expanding scaffold includes a shape memory material or a superelastic material that is elongatable without permanent deformation.

In Example 8, the assembly of any one or any combination of Examples 1-7 can optionally be configured such that the self-expanding scaffold includes a plurality of cutting elements configured to cut into or score the stenotic region within the vessel.

In Example 9, the assembly of any one or any combination of Examples 1-8 can optionally be configured such that the self-expanding scaffold, when in the expanded configuration, is configured to receive an expandable member of a catheter.

In Example 10, the assembly of Example 9 can optionally be configured such that the self-expanding scaffold includes a plurality of braid members or a coil member. A size and shape of each braid member or the coil member can resist bending and apply expandable member force to the stenotic region.

In Example 11, the assembly of any one or any combination of Examples 1-10 can optionally be configured such that the deployment member is a dilator or a stylet.

In Example 12, the assembly of any one or any combination of Examples 1-11 can optionally be configured such that the deployment member includes an inner lumen having a diameter in a range of about 0.014 in to about 0.018 in, inclusive, and an outer surface diameter in a range of about 0.020 in to about 0.030 in, inclusive.

In Example 13, the assembly of any one or any combination of Examples 1-12 can optionally further comprise coupling means between a portion of the elongate push structure and a portion of the deployment member. The coupling means can secure the self-expanding scaffold in the downsized configuration.

In Example 14, the assembly of any one or any combination of Examples 1-13 can optionally further comprise a recovery tube configured to be advanced over the self-expanding scaffold to radially downsize the self-expanding scaffold from the expanded configuration.

In Example 15, an assembly can comprise a scoring member, a deployment member, and means for detachably engaging the deployment member and the scoring member. The scoring member can include an elongate push structure and a self-expanding scaffold. The elongate push structure can be positioned proximal of the self-expanding scaffold and have sufficient rigidity to be pushed distally and pulled proximally to manipulate the expandable scaffold. A proximal end portion of the self-expanding scaffold can include an opening into a central lumen of the self-expanding scaffold. The deployment member can be slidably received within the central lumen of the self-expanding scaffold and used to axially elongate the self-expanding scaffold resulting in a downsized configuration.

In Example 16, the assembly of Example 15 can optionally be configured such that the means for detachably engaging the deployment member and the scoring member includes a funnel structure on the self-expanding scaffold that is sized and shaped to receive a distal end portion of the deployment member.

In Example 17, the assembly of any one or any combination of Examples 15 or 16 can optionally be configured such that the means for detachably engaging the deployment member and the scoring member includes a releasable latch member between a proximal end portion of the elongate push structure and a proximal end portion of the deployment member.

In Example 18, the assembly of any one or any combination of Examples 15-17 can optionally be configured such that the self-expanding scaffold is movable between the downsized configuration, when receiving axial tension from the deployment member, and an expanded configuration, in the absence of axial tension.

In Example 19, a method for scoring a stenotic region within a vessel of a patient can comprise accessing the vessel by piercing an opening; inserting a guidewire into the opening and advancing the guidewire toward or past the stenotic region; inserting a delivery sheath into the vessel; advancing an assembly for scoring the stenotic region through the delivery sheath and toward the stenotic region, the assembly including a self-expanding scaffold and a deployment member positioned within a central lumen of the self-expanding scaffold, the deployment member applying axial tension to a self-expanding scaffold thereby maintaining a radially downsized configuration; removing the deployment member from the self-expanding scaffold, including allowing the self-expanding scaffold to expand from the radially downsized configuration to a radially expanded configuration; advancing a deflated first dilatation balloon of a first catheter over the guidewire and into the central lumen of the self-expanding scaffold; and inflating the first dilatation balloon to press against the interior of the self-expanding scaffold and urge the outer surface of the self-expanding scaffold into the stenotic region.

In Example 20, the method of Example 19 can optionally be configured such that advancing the assembly for scoring the stenotic region through the delivery sheath and toward the stenotic region includes inserting the deployment member over the guidewire.

In Example 21, the method of any one or any combination of Examples 19 or 20 can optionally be configured such that, prior to removal of the deployment member from the self-expanding scaffold, the self-expanding scaffold fully receives the deployment member and a latch member located on each of a proximal end portions of the deployment member and a proximal end portion of an elongate push structure, which is coupled to the self-expanding scaffold, are engaged.

In Example 22, the method of any one or any combination of Examples 19-21 can optionally be configured such that advancing the deflated first dilatation balloon of the first catheter into the central lumen includes advancing the deflated first dilatation balloon through an angled opening at a proximal end portion of the self-expanding scaffold.

In Example 23, the method of any one or any combination of Examples 19-22 can optionally be configured such that inflating the first dilatation balloon includes scoring the stenotic region a first amount.

In Example 24, the method of Example 23 can optionally be configured such that scoring the stenotic region the first amount includes defining a focal point or a radial plane of fracture of the stenotic region and inhibiting its recoil.

In Example 25, the method of Example 23 can optionally further comprise deflating and removing the first dilatation balloon from the vessel; advancing a deflated second dilatation balloon of a second catheter over the guidewire and into the central lumen of the self-expanding scaffold; and inflating the second dilatation balloon to press against the interior of the self-expanding scaffold and urge the outer surface of the self-expanding scaffold into the stenotic region, including scoring the stenotic region a second amount greater than the first amount.

In Example 26, the method of any one or any combination of Examples 19-25 can optionally further comprise advancing a recovery tube over the self-expanding scaffold to urge the self-expanding scaffold to the radially downsized configuration from the radially expanded configuration; and removing the recovery tube and the self-expanding scaffold from the vessel.

Certain terms are used throughout this patent document to refer to particular features or components. As one skilled in the art appreciates, different persons may refer to the same feature or component by different names. This patent document does not intend to distinguish between components or features that differ in name but not in function.

For the following defined terms, certain definitions shall be applied, unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The phrases "target location" or "stenotic region" within a vessel refers to a diseased location or a location suspected of being diseased; in the case of vascular treatment, the target locations will usually be stenotic regions where blood flow is restricted as a result of atheroma deposits or plaque. The terms "distal" and "proximal" are used to refer to a position or direction relative to the treating clinician. "Distal" and "distally" refer to a position that is distant from, or in a direction away from, the treating clinician. "Proximal" and "proximally" refer to a position that is near, or in a direction toward, the treating clinician.

The scope of the present assemblies and methods should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. An assembly for scoring a stenotic region within a vessel, comprising:
   a scoring member including an elongate push structure and a tubular, self-expanding scaffold, the elongate push structure positioned proximal of the self-expanding scaffold and, at its distal end portion, eccentrically coupled with a proximal end portion of the self-expanding scaffold; and
   a deployment member positionable within a central lumen of the self-expanding scaffold, a distal portion of the deployment member insertable into and removable from the central lumen and detachably engageable within the central lumen with a portion of the self-expanding scaffold to apply an axial tension to the self-expanding scaffold when received within the central lumen to move the self-expanding scaffold to a downsized configuration,
   the self-expanding scaffold movable between the downsized configuration, facilitating insertion of the scoring member into the vessel when receiving the axial tension from the deployment member, and an expanded configuration, facilitating contact with the stenotic region in the absence of the axial tension, wherein the deployment member selectively moves the self-expanding scaffold to the downsized configuration.

2. The assembly of claim 1, wherein the proximal end portion of the self-expanding scaffold includes an angled opening sized and shaped to receive a distal end portion of a dilatation balloon when the self-expanding scaffold is positioned within the vessel.

3. The assembly of claim 1, wherein a distal end portion of the self-expanding scaffold includes a funnel sized and shaped to receive, and detachably engage, a distal end portion of the deployment member.

4. The assembly of claim 1, wherein a distal end portion of the self-expanding scaffold includes a first member sized and shaped to detachably engage a second member of a distal end portion of the deployment member.

5. The assembly of claim 1, wherein the self-expanding scaffold includes a plurality of braid members or a coil member, and wherein the braid members or the coil member maintain a more parallel relationship with a longitudinal axis of the scoring member in the downsized configuration than in the expanded configuration.

6. The assembly of claim 1, wherein the self-expanding scaffold includes a shape memory material or a superelastic material that is elongatable without permanent deformation.

7. The assembly of claim 1, wherein the self-expanding scaffold, when in the expanded configuration, is configured to receive a distal end portion of a dilatation balloon.

8. The assembly of claim 7, wherein the self-expanding scaffold includes a plurality of braid members or a coil member, and wherein a size and shape of each braid member or the coil member resists bending and applies dilatation balloon force to the stenotic region.

9. The assembly of claim 1, wherein the deployment member is a dilator or a stylet.

10. The assembly of claim 1, wherein the deployment member includes an inner lumen having a diameter in a range of 0.014 in to 0.018 in, inclusive, and an outer surface diameter in a range of 0.020 in to 0.030 in, inclusive.

11. The assembly of claim 1, further comprising coupling means between a portion of the elongate push structure and a portion of the deployment member, the coupling means securing the self-expanding scaffold in the downsized configuration.

12. The assembly of claim 1, further comprising a recovery tube configured to be advanced over the self-expanding scaffold to transform the self-expanding scaffold from the expanded configuration to the downsized configuration.

13. An assembly, comprising:
   a scoring member including an elongate push structure and a self-expanding scaffold, the elongate push structure positioned proximal of the self-expanding scaffold and having sufficient rigidity to be pushed distally and pulled proximally to manipulate the self-expanding scaffold,
   a proximal end of the self-expanding scaffold including an opening into a central lumen of the self-expanding scaffold;
   a deployment member slidably received through the opening and within the central lumen of the self-expanding scaffold, a distal portion of the deployment member detachably connected to a portion of the self-expanding scaffold within the central lumen, wherein axial tension from the deployment member on the self-expanding scaffold axially elongates the self-expanding scaffold to move the self-expanding scaffold to a downsized configuration; and means for detachably engaging the deployment member and the scoring member.

14. The assembly of claim 13, wherein the means for detachably engaging the deployment member and the scoring member includes a funnel on the self-expanding scaffold that is sized and shaped to detachably engage a distal end portion of the deployment member.

15. The assembly of claim 13, wherein the means for detachably engaging the deployment member and the scoring member includes a releasable latch member between a proximal end portion of the elongate push structure and a proximal end portion of the deployment member.

16. The assembly of claim 13, wherein the self-expanding scaffold is movable between the downsized configuration when receiving axial tension from the deployment member, and an expanded configuration in the absence of axial tension.

17. A method for scoring a stenotic region within a vessel, comprising:

accessing the vessel by piercing an opening;

inserting a guidewire into the opening and advancing the guidewire toward or past the stenotic region;

inserting a delivery sheath into the vessel;

advancing an assembly for scoring the stenotic region through the delivery sheath and toward the stenotic region, the assembly including an elongate push structure positioned proximal of a self-expanding scaffold and a deployment member partially positioned within a central lumen of the self-expanding scaffold, a distal portion of the deployment member detachably engageable with a portion of the self-expanding scaffold within the central lumen, and applying an axial tension to the self-expanding scaffold to move the self-expanding scaffold to a radially downsized configuration;

removing the deployment member from the self-expanding scaffold, including allowing the self-expanding scaffold to transform from the radially downsized configuration to a radially expanded configuration;

advancing a deflated first dilatation balloon of a first catheter over the guidewire and into the central lumen of the self-expanding scaffold; and inflating the first dilatation balloon to press against the interior of the self-expanding scaffold and urge the outer surface of the self-expanding scaffold into the stenotic region.

18. The method of claim 17, wherein inflating the first dilatation balloon includes scoring the stenotic region a first amount.

19. The method of claim 18, wherein scoring the stenotic region the first amount includes defining a focal point or a radial plane of fracture of the stenotic region to inhibit its recoil.

20. The method of claim 18, further comprising:

deflating and removing the first dilatation balloon from the vessel;

advancing a deflated second dilatation balloon of a second catheter over the guidewire and into the central lumen of the self-expanding scaffold; and inflating the second dilatation balloon to press against the interior of the self-expanding scaffold and urge the outer surface of the self-expanding scaffold into the stenotic region, including scoring the stenotic region a second amount greater than the first amount.

21. The method of claim 17, further comprising:

advancing a recovery tube over the self-expanding scaffold to urge the self-expanding scaffold to the radially downsized configuration from the radially expanded configuration; and removing the recovery tube and the self-expanding scaffold from the vessel.

\* \* \* \* \*